United States Patent [19]
Weir

[11] Patent Number: 5,183,035
[45] Date of Patent: Feb. 2, 1993

[54] ORAL HYGIENE DEVICE

[76] Inventor: Roy A. Weir, 940 Lauder Ave., Apt. 914, Toronto, Ontario, Canada

[21] Appl. No.: 796,552

[22] Filed: Nov. 22, 1991

[51] Int. Cl.[5] .............................................. A61H 7/00
[52] U.S. Cl. ........................................ 128/66; 433/80
[58] Field of Search ............................ 128/66; 433/80

[56] References Cited

U.S. PATENT DOCUMENTS

| | | | |
|---|---|---|---|
| 3,736,923 | 6/1973 | Parkison | 128/66 |
| 4,223,668 | 9/1980 | Lamy et al. | 128/66 |
| 4,596,058 | 6/1986 | Nourbakhsh | 128/66 |
| 4,991,570 | 2/1991 | Bullard | 128/66 |

Primary Examiner—John J. Wilson
Attorney, Agent, or Firm—Kenneth M. Garrett

[57] ABSTRACT

An oral hygiene device comprises a bowl, a handle and a lid hinged to the bowl. Water is connected to the device by a small hose, and a drainage hose is provided. A valve is interconnected with the lid to initiate the flow of flushing water into the bowl when the lid opens. A manually operable valve is operable to provide a fountain of rinsing water. A mouth wash fountain may also be provided. The lid is upwardly dished to provide an interior compartment closed off by a mirror which is hinged to provide access to the compartment. A light may also be provided in the compartment. A pump is provided for emptying drainage water. The device may be used out of the bathroom by bedridden patients.

17 Claims, 4 Drawing Sheets

ORAL HYGIENE DEVICE

FIELD OF INVENTION

This invention relates to a device useful in promoting oral hygiene.

BACKGROUND OF INVENTION

It particularly relates to a device that may be hand held and used outside of close proximity to bathroom facilities whereby it may have a particular use with bed-ridden persons, although it is not restricted thereto.

SUMMARY OF INVENTION

In accordance with one aspect of my invention, an oral hygiene device comprises a bowl portion having a rim therearound and a handle portion disposed at one radial side of the bowl portion for manually supporting the device A lid is hingedly secured to one of these portions so as to be movable between a raised position, to provide access to the interior of the bowl portion and a lowered position to generally enclose the interior.

The device also includes a first conduit for supplying a stream of water directed generally below the level of the rim for flushing the interior of the bowl portion, and a second conduit for supplying a stream of upwardly upwardly directed water from adjacent the rim portion into the bowl portion. First and second valve means are also provided for respectively controlling the flow of water through the first and second conduits, and a drainage opening is disposed in the bottom of the bowl portion.

Suitably the valve means is operatively connected to the lid so as to be opened when the lid is moved to its raised position, and closed when the lid is moved to its lowered position.

Typically, the device will include a base portion for supporting the device from the surface when not in use and the base portion will interconnect the bowl portion and the handle portion, and a drainage tube will be contained within the base portion connected to the drainage opening.

Also typically my oral hygiene device will further comprise an entry port disposed in the handle portion, and wherein the drainage tube will be disposed within the entry port. A fresh water supply tube will also be disposed with the entry port and interconnected with the first and second conduits.

Preferably, my oral hygiene device will comprise a conduit means for delivering a stream of mouth rinse upwardly directed above the rim of the bowl portion, and a third valve means operatively connected to control the flow of mouth rinse.

As a still further refinement which may be used to facilitate the provision of mouth rinse and the drainage of waste water from the device, electric pumps may be provided and control valves therefor, which may be in the form of electrical switches. Suitable, the switch controlling the drainage pump may be operatively interconnected with the lid so as to switch the drainage pump between an ON and an OFF condition respectively as the lid is raised and lowered.

Preferably my device will include a flexible tube connected into the entry port, within which tube there is contained at least a fresh water supply hose and a drainage hose for the device, and the electrical wiring for the device. The lid of my oral hygiene device typically has an upwardly dished interior, and the device will further comprise a mirror at least partially enclosing the dished interior. A translucent sheet member may also be provided which, together with the mirror, may substantially completely enclose the dished interior suitably, at least one of the mirror and the translucent sheet member is hingedly mounted from the lid to be moveable between a first position generally enclosing the dished interior and a second position providing access to the dished interior. A lamp means is preferably contained in the dished interior, and a lid actuated switch will be provided to switch the lamp means ON and OFF respectively as the lid is raised and lowered.

These foregoing objects and aspects of the invention, together with other objects, aspects and advantages thereof will be more apparent from the following description of a preferred embodiment thereof, taken in conjunction with the following drawings.

DESCRIPTION OF THE PREFERRED EMBODIMENT

Figure 1:
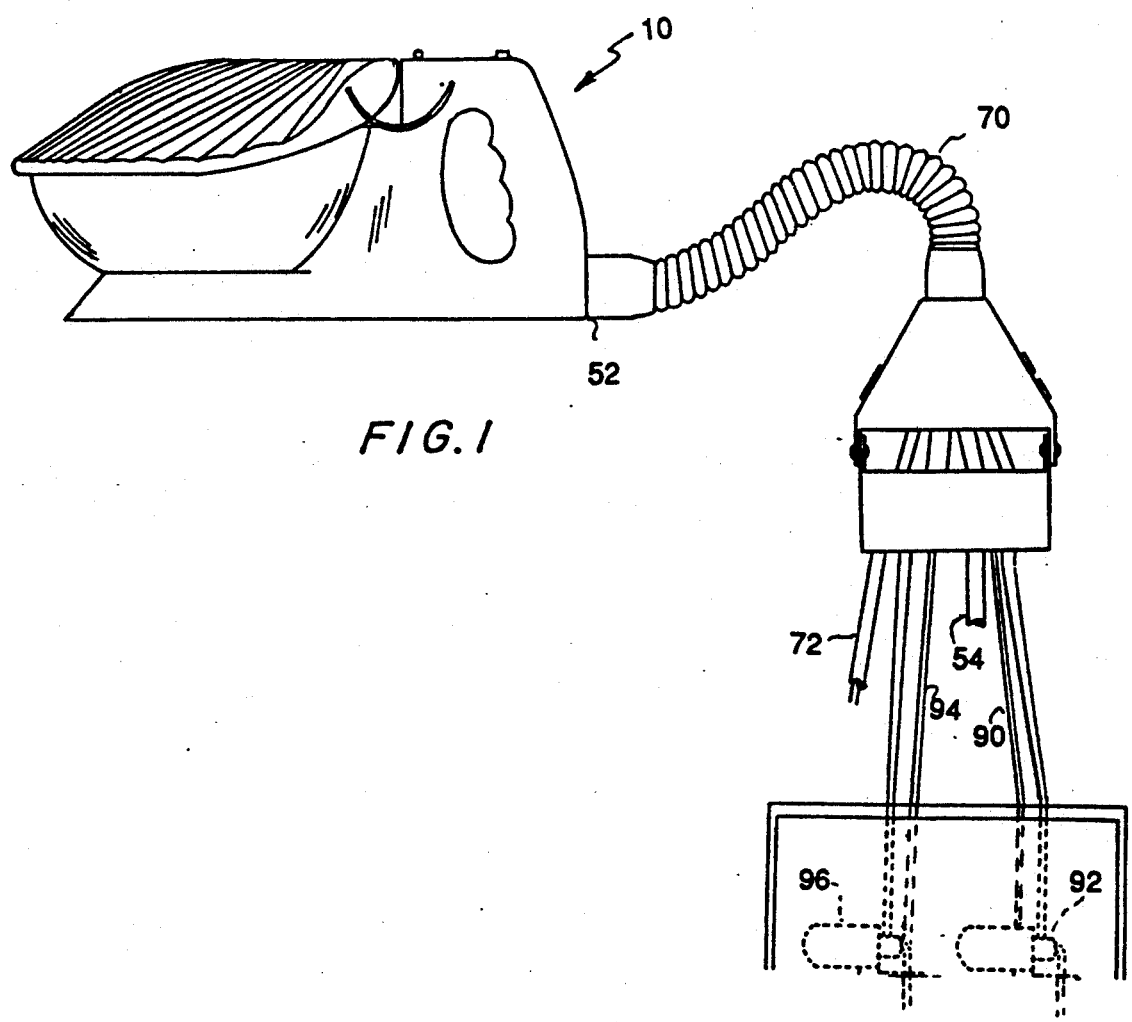
FIG. 1—shows the oral hygiene device of my invention in side elevation.
Figure 2:
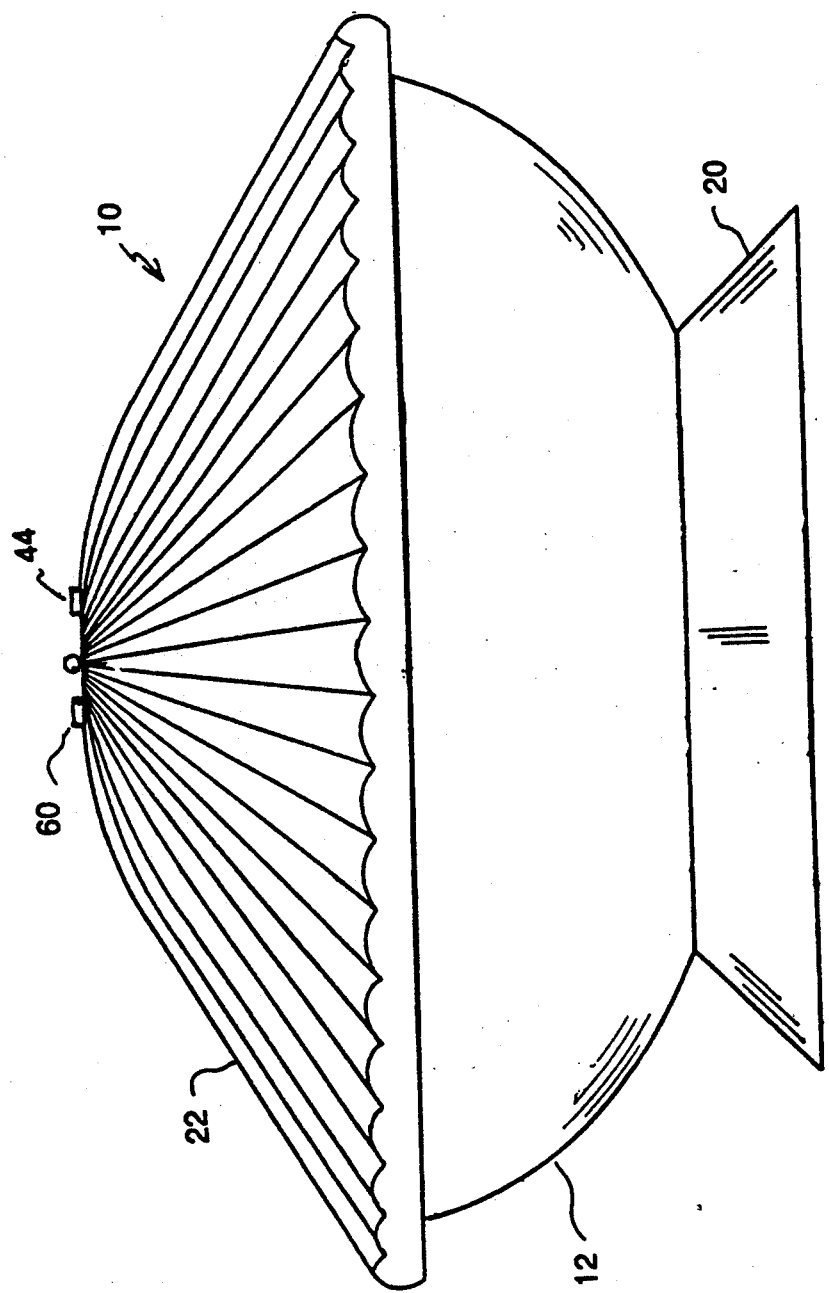
FIG. 2—shows the device of FIG. 1 in front elevation.
Figure 3:
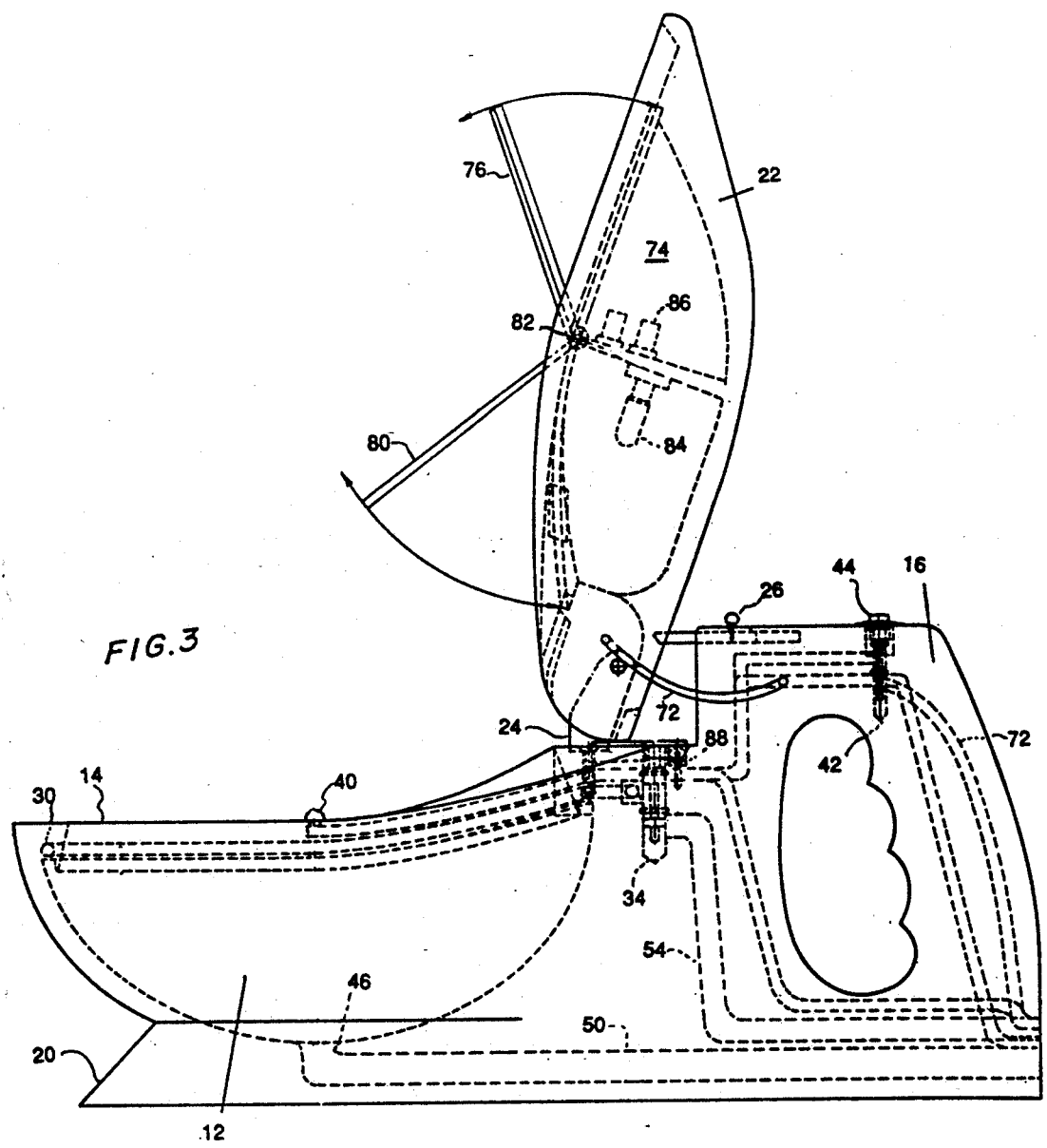
FIG. 3—shows the device of FIG. 1 in side elevation with the lid thereof in its open position and other hinged parts in their open position, with hidden detail shown in dashed outline, and FIG. 4—shows the device of FIG. 1 in top plan view, with the lid removed, and with hidden detail shown in dashed outline.
Figure 4:
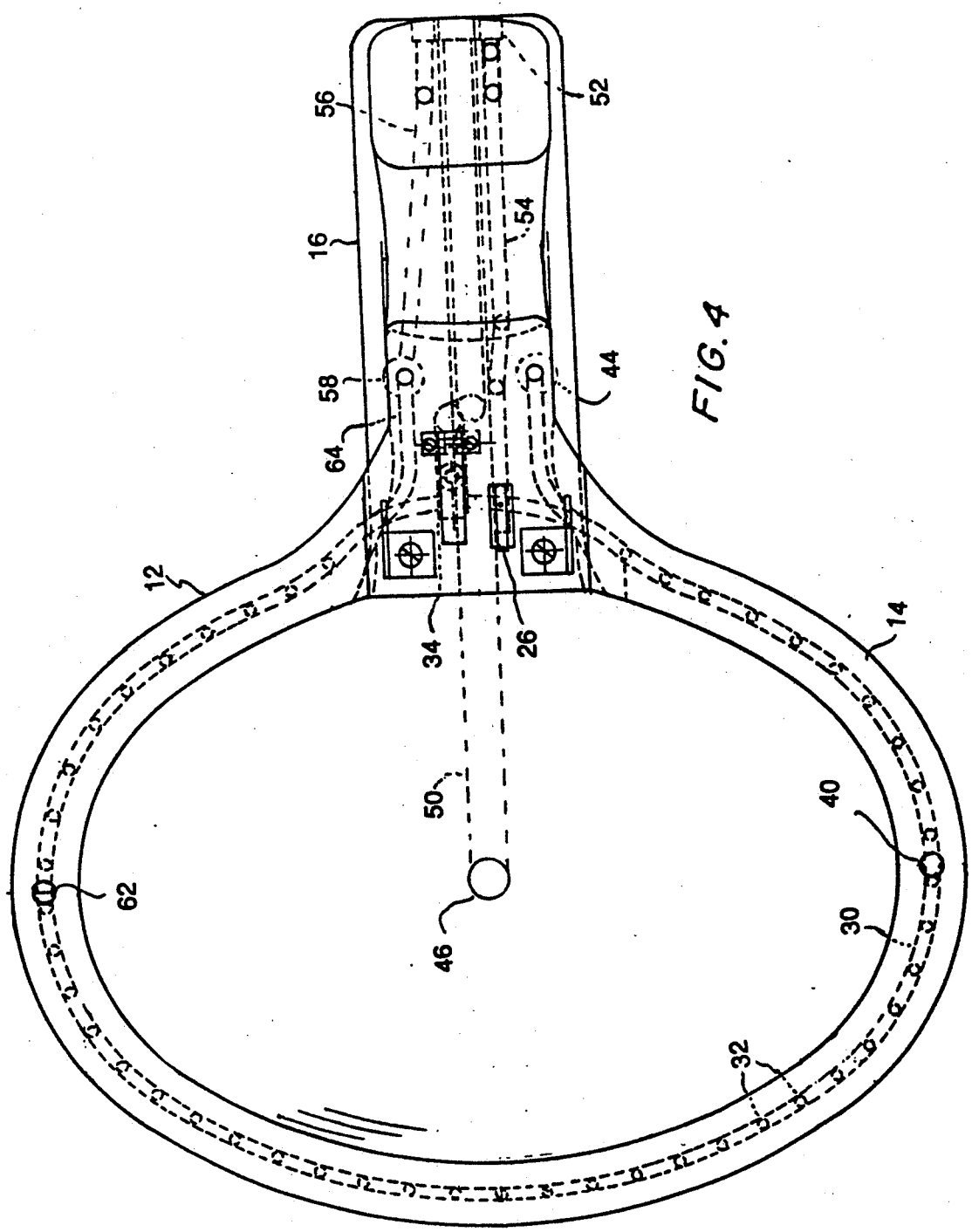

Referring to the drawings in detail, the oral hygiene device of my invention is identified generally therein by the number 10. Oral hygiene device 10 comprises a bowl portion 12 having a rim 14 therearound in a generally horizontal plane as the device is normally employed, a handle portion 16 disposed on a diameter of the bowl portion rearwardly thereof, and a base 20 which interconnects the bowl and handle portions. Oral hygiene device 10 further comprises a lid 22 which is hinged to the bowl portion 12 adjacent the juncture thereof with handle portion 16 by hinge 24 so as to be movable between a first lowered position, seen in FIG. 2, wherein it encloses the interior of the bowl portion, and a second open position, seen in FIG. 3 to give access to the interior of the bowl portion. A latch 26 is provided to retain lid 22 in its open position.

A water conduit 30 is provided within bowl portion 12 adjacent the rim 14 thereof, which conduit completely circumscribes the interior of the bowl portion. Water conduit 30 is provided with a plurality of downward openings 32 therearound, so as to provide a curtain of water over the interior surface of the bowl portion 12 when the conduit is connected to a water supply.

Conduit 30 is connected in flow relation to a normally OFF shut-off valve 34, which is actuated to an ON position by opening lid 22, and to its OFF position upon closure of the lid. A second conduit 36 is provided which locates marginally above water conduit 30, and which terminates at an upwardly directed jet 40 locating on a diameter generally transverse to that containing handle portion 16. Conduit 36 connects in flow relation to a second normally OFF shut-off valve 42, the actuator therefor comprising a push button 44 locating the top of handle portion 16.

A drainage opening 46 is disposed in bottom of the bowl portion 12, and a drainage tube 50 disposed in base 20 connects the drainage opening to an entry port 52 located at the rear of handle portion 16. A fresh water supply tube 54 is also disposed in entry port 52 and is connected in flow relationship with the shut-off valves 34,42. A mouth-rinse supply tube 56 is also disposed in entry port 52, which tube is connected within the handle port to a third, normally OFF shut-off valve 58. Valve 58 is actuatable to the ON position by a push button 60 located on the top of handle portion 16, and connects to an upwardly directed jet 62 generally diametrically opposed to jet 40 by means of a conduit 64.

A lightly armoured flexible tube 70 connects to entry port 52, within which tube is contained hoses to interconnect the fresh water and mouth rinse supply tubes 54, 56 to a supply source, not shown, and to connect the drainage tube 50 to a suitable drain. An electric cord 72 also locates within tube 70 to furnish a supply of low voltage power to device 10.

Lid 22 has an upwardly dished interior 74; the upper portion of the dished interior, as viewed with the lid in its open position is enclosed by a mirror 76 while the lower portion is enclosed by a translucent plastic material 80, each of which is hinged to lid 22 along a transverse axis 82 to be operable to gain access to the dished interior of the lid. A lamp 84 is mounted behind sheet material 80, and tooth brush holders 86 are mounted behind mirror 76. Lamp 84 is serially connected to electrical cord 72 by means of normally off switch 88, which is activated to an ON condition by the opening of lid 22. A second electrical cord 90 contained within tube 70 is connected in parallel relation with lamp 84 and serves to provide power to a small pump 92, which serves to empty drainage tube 50. A third electrical cord 94 contained within tube 70 is connected in parallel relation with lamp 84 and a normally closed switch operated to the ON position by actuation of push button 60, cord 94 serving to supply power to a small pump 96 for the purpose of dispensing mouth rinse from a supply (not shown) thereof.

It is believed that the operation of the oral hygiene device 10 of the invention will be apparent from the foregoing description thereof.

Typically, the device is used when held by handle portion 16. Lid 22 is opened, thereby switching lamp 84 ON, opening water supply shut-off valve 34 and supply power to a drainage pump. A fresh water mouth wash is obtained by actuating push button 44, thereby providing a flow of water upwardly directed from jet 40 above rim 14. Similarly a mouth rinse jet is obtained by actuating push button 60. Should it be desired, the fresh water for the mouth wash can be separate from the supply of water for rinsing the device, in which case the supply of fresh water may be treated in the same manner as the mouth rinse.

It will be apparent that many changes may be made to the illustrative embodiments, while falling within the scope of the invention and it is intended that all such changes be covered by the claims appended hereto.

I claim:

1. An oral hygiene device comprising:
    a bowl portion having a rim therearound and
    a handle portion disposed at one radial side of the bowl portion for manually supporting the device;
    a lid hingedly secured to one of said portions so as to be movable between a raised position to provide access to the interior of said bowl portion and a lowered position to generally enclose said interior;
    a first conduit for supplying a stream of water directed generally below the level of said rim for flushing the interior of said bowl portion;
    a second conduit for supplying a stream of upwardly directed water;
    first and second valve means for respectively controlling the flow of water through said first and second conduits, and
    a drainage opening disposed in the bottom of said bowl portion.

2. An oral hygiene device as defined in claim 1, wherein said first valve means is operatively connected to said lid so as to be opened when said lid is moved to said raised position and closed when said lid is moved to said lowered position.

3. An oral hygiene device as defined in claim 1, further comprises
    a base portion for supporting said device, said base portion interconnecting said bowl portion and said handle portion, and
    a drainage tube contained within said base portion connected to said drainage opening.

4. An oral hygiene device as defined in claim 3, further comprising an entry port disposed in said handle portion, and wherein said drainage tube is disposed within said entry port.

5. An oral hygiene device as defined in claim 4, further comprising a fresh water supply tube disposed within said entry port and interconnected with said first and second conduits.

6. An oral hygiene device as defined in claim 1, further comprising conduit means for delivering a stream of mouth rinse upwardly directed above the rim of said bowl portion.

7. An oral hygiene device as defined in claim 6, further comprising third valve means operatively connected to control the flow of mouth rinse.

8. An oral hygiene device as defined in claim 7, further comprising a first electrically driven pump for delivery mouth rinse to said conduit means and wherein said third valve means is an electric switch operatively connected to said electric pump.

9. An oral hygiene device as defined in claim 7, further comprising a second electrically driven pump for draining liquid from said drainage tube, and a fourth valve means is provided comprising an electric switch operatively connected to said second pump.

10. An oral hygiene device as defined in claim 9, wherein said fourth valve means is operatively interconnected with said lid so as to switch said second pump between an ON and an OFF condition respectively as said lid is raised and lowered.

11. An oral hygiene device as defined in claim 1, further comprising a flexible tube connected into said entry port within which tube there is contained at least a fresh water supply hose and a drainage hose for said device.

12. An oral hygiene device as defined in claim 1, wherein said lid has an upwardly dished interior, and further comprising a mirror at least partially enclosing said dished interior.

13. An oral hygiene device as defined in claim 12, further comprising a translucent sheet member which together with said mirror, substantially completely encloses said dished interior.

14. An oral hygiene device as defined in claim 13, wherein at least one of said mirror and said translucent sheet member is hingedly mounted from said lid to be moveable between a first position generally enclosing said dished interior and a second position providing access to said dished interior.

15. An oral hygiene device as defined in claim 14, wherein each of said mirror and said translucent sheet member is hingedly mounted from said lid.

16. An oral hygiene device as defined in claim 14, further comprising lamp means located within said dished interior.

17. An oral hygiene device as defined in claim 16, further comprising normally closed electrical switch means serially connected with said lamp means, and wherein said lid when in its raised position actuates said switch means to an ON position.

* * * * *